US012576143B2

(12) United States Patent
Nicosia et al.

(10) Patent No.: US 12,576,143 B2
(45) Date of Patent: Mar. 17, 2026

(54) TELEOST INVARIANT CHAIN CANCER VACCINE

(71) Applicant: NOUSCOM AG, Basel (CH)

(72) Inventors: Alfredo Nicosia, Naples (IT); Elisa Scarselli, Rome (IT); Armin Lahm, Rome (IT)

(73) Assignee: NOUSCOM AG, Basel (CH)

( * ) Notice: Subject to any disclaimer, the term of this patent is extended or adjusted under 35 U.S.C. 154(b) by 598 days.

(21) Appl. No.: 17/281,942

(22) PCT Filed: Oct. 18, 2019

(86) PCT No.: PCT/EP2019/078395
§ 371 (c)(1),
(2) Date: Mar. 31, 2021

(87) PCT Pub. No.: WO2020/079234
PCT Pub. Date: Apr. 23, 2020

(65) Prior Publication Data
US 2021/0379169 A1 Dec. 9, 2021

(30) Foreign Application Priority Data
Oct. 19, 2018 (EP) .................................... 18201541

(51) Int. Cl.
| | |
|---|---|
| *C07K 14/46* | (2006.01) |
| *A61K 39/00* | (2006.01) |
| *A61K 39/385* | (2006.01) |
| *A61K 40/42* | (2025.01) |

(52) U.S. Cl.
CPC ... *A61K 39/001114* (2018.08); *A61K 39/0011* (2013.01); *A61K 39/385* (2013.01); *A61K 40/4201* (2025.01); *A61K 40/4213* (2025.01); *C07K 14/461* (2013.01); *A61K 2039/5256* (2013.01); *A61K 2039/53* (2013.01); *A61K 2039/605* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 11,912,743 B2 * | 2/2024 | Nicosia .................. | C12N 15/86 |
| 2011/0293704 A1 | 12/2011 | Holst et al. | |

FOREIGN PATENT DOCUMENTS

| | | | |
|---|---|---|---|
| EP | 17200036.6 | * | 3/2017 |
| EP | 17211235.1 | * | 12/2017 |
| JP | 2017-131220 A | | 8/2017 |
| WO | 1996/005309 | | 2/1996 |
| WO | 2009/091912 | | 7/2009 |
| WO | 2015/082922 | | 6/2015 |
| WO | 2018/037045 | | 3/2018 |
| WO | WO-2019086615 A1 * | 5/2019 | ............. A61K 38/00 |

OTHER PUBLICATIONS

Alberts et al. (Molecular Biology of the Cell. 4th edition, New York: Garland Science; 2002; retrieved from http://www.ncbi.nlm.nih.gov/books/NBK26917/ on Mar. 2, 2015, 10 pages) (Year: 2002).*

Bandola-Simon et al. ('Defective removal of invariant chain peptides from MHC class II suppresses tumor antigen presentation and promotes tumor growth' Cell Reports v44 Jan. 28, 2025 pp. 1-14) (Year: 2025).*

HLA class II histocompatibilityantigen gamma chain-like isoform X2 [Boleophthalmuspectinirostris], NCBI Reference Sequence [online], Accession No. XP_020777661 (Apr. 29, 2017).

The International Search Report (ISR) with Written Opinion for PCT/EP2019/078395 Jan. 16, 2020, pp. 1-19.

Database UniParc [Online] Feb. 9, 2017 (Feb. 9, 2017) XP002790489, retrieved from UniProt Database accession No. UPI00097CEAEO the whole document.

Database UniParc [Online] Apr. 30, 2017 (Apr. 30, 2017) XP002790490, retrieved from UniProt Database accession No. UPIOOOA1C2E91 the whole document.

Capone, Stefania et al. Fusi on of HCV nonstructural antigen to MHC class II-associated invariant chain enhances T-cell responses induced by vectored vaccines in nonhuman primates: Molecular Therapy (2014) vol. 22(5), pp. 1039-1047.

Spencer, Alexandra J. et al. "Enhanced vaccine-induced CD8+ T cell responses to malaria antigen ME-TRAP by fusion to MHC class ii invariant chain" PLOS One (2014) vol. 9(6), pp. 1-15.

NCBI Reference Sequence: XP_020777629.1, Apr. 2017.

NCBI Reference Sequence XP019944063.1, Predicted: uncharacterized protein LOC109630345, Feb. 2017.

NCBI Reference Sequence: XP_020777660.1, Apr. 2017.

NCBI Reference Sequence: XP_019944063.1, Feb. 2017.

* cited by examiner

*Primary Examiner* — Ronald T Niebauer
(74) *Attorney, Agent, or Firm* — McDonnell Boehnen Hulbert & Berghoff LLP

(57) ABSTRACT

The present invention relates to polypeptides comprising a fragment of a teleost invariant chain optionally fused to one or more antigens or a teleost invariant chain fused to one or more antigens or antigenic fragments thereof, a polynucleotide encoding such polypeptides, vectors comprising such polynucleotides, collection of vectors comprising such polynucleotides and use of such polypeptides, polynucleotides, vectors for treating or preventing diseases, in particular tumor diseases. The teleost invariant chain polypeptides or fragments thereof act as "T cell enhancer" converting non-immunogenic antigenic sequences into immunogenic T cell antigens.

9 Claims, 1 Drawing Sheet

Specification includes a Sequence Listing.

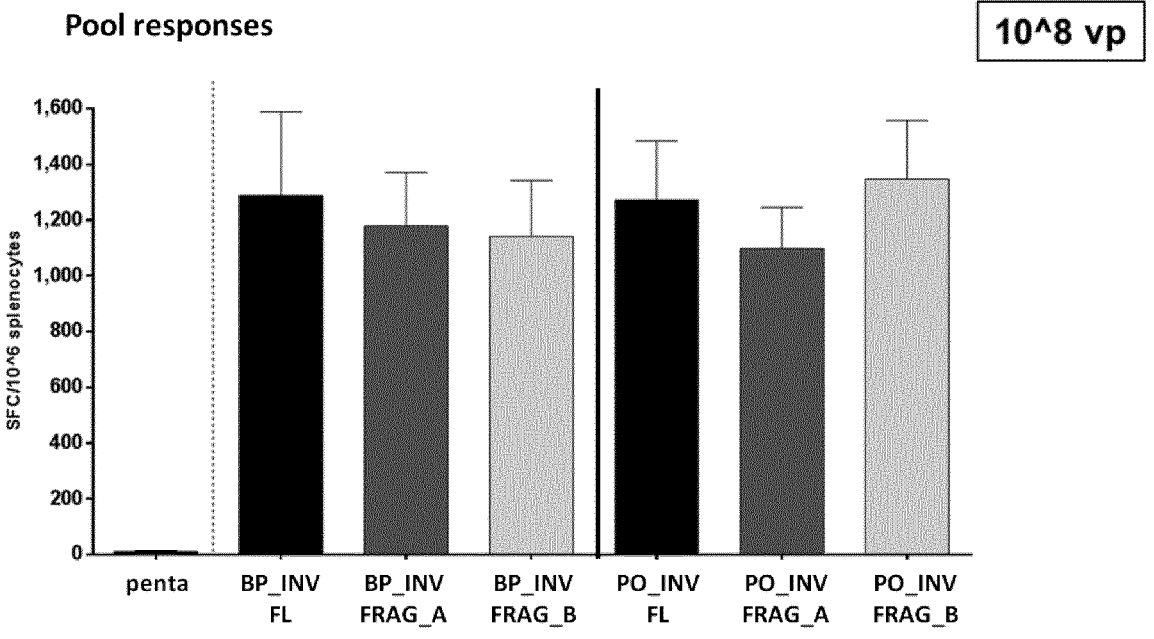

TELEOST INVARIANT CHAIN CANCER VACCINE

CROSS REFERENCE TO RELATED APPLICATION

This application is a U.S. national phase of International Application No. PCT/EP2019/078395, filed Oct. 18, 2019, which claims priority to European Patent Application No. 18201541.2, filed Oct. 19, 2018, both of which are incorporated by reference herein in their entirety.

The present invention relates to polypeptides comprising a fragment of a teleost invariant chain optionally fused to one or more antigens or a teleost invariant chain fused to one or more antigens or antigenic fragments thereof, a polynucleotide encoding such polypeptides, vectors comprising such polynucleotides, collection of vectors comprising such polynucleotides and use of such polypeptides, polynucleotides, vectors for treating or preventing a proliferative disease, preferably cancer, viral disease, fungal disease or bacterial disease. The teleost invariant chain polypeptides or fragments thereof act as "T cell enhancer" converting non-immunogenic antigenic sequences into immunogenic T cell antigens.

BACKGROUND OF THE INVENTION

Sometimes vaccines elicit a suboptimal or no T-cell immune response. This phenomenon of poor induction of T-cell immune response is more frequently observed in case of vaccinations that target antigens that are either fully self molecules, e.g. cancer-specific antigens, or partially self, e.g. cancer-specific neoantigens. Cancer-specific neoantigens mostly derive from point mutations in coding regions of genes, which lead to non-synonymous single nucleotide variants resulting in the change of one amino acid. A single amino acid change in a protein sequence very rarely generates a novel epitope able to induce a potent immune response. In most cases, this small change either does not generate a novel epitope at all or may generate a very weak one. Because of pre-existing central tolerance against self antigens, the induction of potent immune responses against cancer specific antigens through vaccination remains a challenging task. To overcome the lack of or poor immunogenicity of cancer specific antigens and neoantigens, several strategies have been employed to rescue lack/poor immunogenicity of some genetic vaccines. Invariant chain (INV) has been shown to enhance CD8$^+$ T cell induction in the context of genetic vaccination. The invariant chain is a chaperone protein of major histocompatibility complex (MHC) class II molecules, required for their maturation and assembly. INV also plays a role in presenting antigenic peptides and it has been demonstrated to increase induction of T cells when fused to an antigen in the context of genetic vaccination. Improved immunization capacity with a lentiviral vector expressing ovalbumin fused to INV has been described (Rowe et al 2006 Mol Ther 13(2) 310-9). Subsequently, various reports documented enhanced induction of CD8$^+$ T cell responses by human adenovirus 5 and plasmid DNA vectors expressing INV-fused antigens.

In cancer vaccination, it is important to avoid tumor escape through the emergence of novel cancer specific antigens not recognized by vaccine induced T cells. The challenge for a cancer vaccine in curing cancer is to induce a diverse population of immune T cells capable of recognizing and eliminating as large a number of cancer cells as possible at once, to decrease the chance that cancer cells can "escape" the T cell response. Therefore, it is desirable that the vaccine encodes quite a large number of cancer specific antigens. This is particular relevant for the recently described personalized vaccine approach based on cancer specific neoantigens. In order to optimize the probability of success as many neoantigens as possible should be targeted by the vaccine, however the maximal insert size of vectors is limited. Full-length INV sequences or large fragments thereof occupy a relatively large portion of the vaccine antigen insert. Therefore, the use of short polypeptide as T cell enhancer is preferable in the context of anti-cancer vaccination especially when using several cancer specific antigens in the vaccine.

Genetic vaccination platforms based on adenovirus, in particular Great Apes derived Adenovirus (GAd) viral vector were shown to be very potent for induction of T cell responses and Great Ape derived Adenoviruses are suitable for encoding large antigens in the format of artificial genes composed of polynucleotides encoding fragments from different proteins linked one after the other (Borthwick, N., et al., Mol Ther, 2014. 22(2): p. 464-75). Unexpectedly, when used in the context of cancer specific neoantigens, no T cell mediated immune response was induced.

The present inventors identified specific INV sequences able to restore immunogenicity. Such INV sequences were suitable in overcoming the lack of or poor immunogenicity of cancer specific neoantigens. In particular two short fragments of a non-human Teleostei INV were identified both not including the transmembrane domain that acted as potent T cell enhancers.

The use of human INVs or of INVs of phylogenetically closely related species may result in undesired induction of an immune response against this self sequence in the context of vaccination. The autoimmune response would be in this case directed towards normal tissues in which INV is expressed. The present inventors have surprisingly found that INVs of teleosts although quite different from mammalian INVs increase the T cell response against antigens in mammalians, that this T cell response enhancing effect is exerted on multiple antigens fused to a teleost invariant chain and that already a short fragment of teleost INV is sufficient to elicit this response. Thus, the present invention provides inter alia: (i) an improved enhancer of T cell response against antigens in mammals, with a decreased likelihood of eliciting unwanted T cell responses against healthy tissue, (ii) an enhancer of T cell response against multiple antigens, and (iii) a short fragment capable of eliciting a T cell that maximizes the ability to fuse a large number of antigens or antigenic fragments thereof.

SUMMARY OF THE INVENTION

In a first aspect of the invention the invention relates to a polypeptide comprising:

(a) a fragment of an invariant chain (INV) of a Teleostei comprising or consisting of between 16 to 27 contiguous amino acids of the membrane proximal domain (MPD) of an INV of the Teleostei, wherein the fragment has T cell response enhancer activity and the MPD is characterized by an amino acid sequence selected from:

(i)
    NQRX$_1$DIKSLEEQX$_2$SX$_3$LX$_4$X$_5$X$_6$X$_7$TX$_8$GRSX$_9$X$_{10}$
    (SEQ ID NO: 001)
    wherein
    X$_1$ is G or N, X$_2$ is H or N, X$_3$ is G or N, X$_4$ is N or Q, X$_5$ is E or A, X$_6$ is Q or E, X$_7$ is L or M, X$_8$ is K or R, X$_9$ is A or V and X$_{10}$ is S or A;

and wherein the fragment is preferably at least 60% identical to SEQ ID NO: 3; or (ii) DQKQQIQZ$_1$LQZ$_2$Z$_3$NQRZ$_4$EKQZ$_5$Z$_6$Z$_7$RZ$_8$RZ$_9$S (SEQ ID NO: 8) wherein Z$_1$ is G or D, Z$_2$ is T or A, Z$_3$ is T or S, Z$_4$ is L or M, Z$_5$ is M or V, Z$_6$ is G or S, Z$_7$ is Q or L, Z$_8$ is P or S, and Z$_9$ is E or V;

and wherein the fragment is preferably at least 60% identical to SEQ ID NO: 10;

and optionally one or more antigens and/or one or more antigenic fragments thereof;

or (b) a full length Teleostei INV selected from SEQ ID NO: 2, 5, 9 or 12, or variants thereof, which has T cell response enhancer activity, wherein the amino acid sequence of the MPD of the variant is at least 60% identical to SEQ ID NO: 3 or 10, and one or more antigens and/or one or more antigenic fragments thereof.

In a second aspect the invention further relates to a polynucleotide encoding the polypeptide according to the first aspect of the invention, wherein the polynucleotide is DNA or RNA, preferably DNA.

In a third aspect the invention relates to a vector comprising the polynucleotide according to the second aspect of the invention.

In a fourth aspect the invention relates to a collection of two or more different vectors, wherein the different vectors each comprise a polynucleotide according to the second aspect of the invention encoding a different polypeptide according to the first aspect of the invention.

In a fifth aspect the invention relates to a pharmaceutical composition comprising the polypeptide of the first aspect of the invention, the polynucleotide of the second aspect of the invention, or a vector/vector collection of the third or fourth aspect of the invention, a pharmaceutically acceptable excipient and optionally one or more adjuvants.

In a sixth aspect the invention relates to a kit of parts comprising the pharmaceutical composition of the fifth aspect of the invention and separately packaged at least one immunomodulatory, or at least one polynucleotide encoding the immunomodulator, or a vector comprising the polynucleotide encoding the immunomodulator.

In a seventh aspect the invention relates to a polypeptide according to the first aspect, a polynucleotide according to the second aspect, a vector or a collection of vectors according to the third or fourth aspect, or a pharmaceutical composition or kits comprising such pharmaceutical compositions according to fifth or sixth aspect for use in preventing or treating a proliferative disease, preferably cancer, viral disease, fungal disease or bacterial disease.

LIST OF FIGURES

In the following, the content of the figures comprised in this specification is described. In this context please also refer to the detailed description of the invention above and/or below.

FIG. 1: Immunogenicity of GAd-penta (penta) and GAd vectors encoding for BP and PO full-length invariant chain (BP_INV FL [SEQ ID NO: 9] and PO_INV_FL [SEQ ID NO: 2]) or fragments FRAG_A (BP_INV FRAG_A [SEQ ID NO: 10] and PO_INV FRAG_A [SEQ ID NO: 3]) and FRAG_B (BP_INV FRAG_B [SEQ ID NO: 11] and PO_INV FRAG_B [SEQ ID NO: 4] thereof) linked to the N-terminus of the penta antigen. Mice (n=5-6/group) were immunized with 10$^8$ vp of each vector and 2 weeks later immune responses were measured by ELISpot assay on spleen. Shown are the average responses (number of T cells producing IFNγ per millions of splenocytes) to a pool of 5 synthetic peptides corresponding to the sequences of the neoantigens encoded in pentatope. Values shown are mean+/–SEM from measurements performed on 5-6 mice/group.

DETAILED DESCRIPTIONS OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland) and as described in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National Formulary-20, published by the United States Pharmcopeial Convention, Inc., Rockville Md., 2001.

Throughout this specification and the claims which follow, unless the context requires otherwise, the word "comprise", and variations such as "comprises" and "comprising", will be understood to imply the inclusion of a stated feature, integer or step or group of features, integers or steps but not the exclusion of any other feature, integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

DEFINITIONS

To practice the present invention, unless otherwise indicated, conventional methods of chemistry, biochemistry, and recombinant DNA techniques are employed which are explained in the literature in the field (cf., e.g., Molecular Cloning: A Laboratory Manual, 2$^{nd}$ Edition, J. Sambrook et al. eds., Cold Spring Harbor Laboratory Press, Cold Spring Harbor 1989).

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term transmembrane domain (TMD) is used in the present invention to refer to the TMD of invariant chain sequences (INVs) is defined as the amino acid segment starting 17 residues N-terminal of the Gln (Q) residue conserved in all INVs and ending 8 residues C-terminally from the conserved Q thus including a total of 26 residues.

The term membrane proximal domain (MPD) is used in the present invention to refer to the segment of 27 residues immediately C-terminal of the TMD of INVs.

The term "adjuvant" is used in the present invention as substances that enhance the immune response to the antigen. In addition adjuvants have also evolved as substances that can help in stabilizing formulations of antigens. Adjuvants are added to vaccines to stimulate the immune system's response to the target antigen, but do not provide immunity themselves. Adjuvants are needed to improve routing and adaptive immune responses to antigens. Adjuvants apply their effects through different mechanisms. For example, by extending the presence of antigen in the blood or/and helping the antigen presenting cells absorb antigen, and/or activating macrophages and lymphocytes and/or supporting the production of cytokines. Some adjuvants, such as alum, function as delivery systems by generating depots that trap antigens at the injection site, providing a slow release that continues to stimulate the immune system. Among described types of adjuvants there are i) Inorganic compounds: alum, aluminum hydroxide, aluminum phosphate, calcium phosphate hydroxide ii) Mineral oil: paraffin oil iii) Bacterial products: killed *Bordetella pertussis* bacteria, *Mycobacterium bovis*, toxoids iv) Nonbacterial organics: squalene, v) Delivery systems: detergents (Quil A), vi, Plant saponins from Quillaja (See *Quillaia*), Soybean, *Polygala senega*, vii) Cytokines: IL-1, IL-2, IL-12, viii) Combination: Freund's complete adjuvant, Freund's incomplete adjuvant.

The term "immunomodulator" is used in the present invention to refer any drug or substance that has an effect on the immune system. An immunomodulator can adjust the immune response to the correct level by: i) strengthen weak immune systems ii) control overactive immune systems.

A particular class of immunomodulators able to strengthen weak immune systems are modulators of immunological check point molecules (MCM) consisting of

6 i) agonistic activator MCMs like a tumor necrosis factor (TNF) receptor superfamily member, preferably of CD27, CD40, OX40, GITR or CD137 ii) antagonistic inhibitory MCMs like PD-1, CD274, A2AR, B7-H3, B7-H4, BTLA, CTLA-4, IDO, KIR, LAG3, TIM-3, VISTA or B7-CD28 superfamily member, CD28 or ICOS or an antagonist of a ligand thereof.

Another class of immunomodulators that can strength a weak immune system are cytokines, which are acting as T cells growth factors. Preferred examples of such cytokines are IL-2, IL-12, IL-15, or IL-17.

The term "antigen" is used in the context of the present invention to refer to any structure recognized by molecules of the immune response, e.g. antibodies, T cell receptors (TCRs) and the like. Preferred antigens are cellular or foreign, e.g. viral bacterial or fungal) proteins that are associated with a particular disease. Antigens are recognized by highly variable antigen receptors (B-cell receptor or T-cell receptor) of the adaptive immune system and may elicit a humoral or cellular immune response. Antigens that elicit such a response are also referred to as immunogen. A fraction of the proteins inside cells, irrespective of whether they are foreign or cellular, are processed into smaller peptides and presented to by the major histocompatibility complex (MHC).

The term "antigenic fragment thereof" refers to a part of a given antigen that is still recognized by a molecule of the immune system. An antigenic fragment will comprise at least one epitope or antigenic determinant. Preferably, the antigenic fragments of the invention comprise at least one T cell epitope.

The term "epitope", also known as antigenic determinant, is used in the context of the present invention to refer to the segment of an antigen, preferably peptide that is bound by molecules of the immune system, e.g. B-cell receptors, T-cell receptors or antibodies. The epitopes bound by antibodies or B cells are referred to as "B cell epitopes" and the epitopes bound by T cells are referred to as "T cell epitopes". In this context, the term "binding" preferably relates to a specific binding, which is defined as a binding with an association constant between the antibody or T cell receptor (TCR) and the respective epitope of $1\times10^5$ M–1 or higher, preferably of $1\times10^6$ M–1, $1\times10^7$ M–1, $1\times10^8$ M–1 or higher. The skilled person is well aware how to determine the association constant (see e.g. Caoili, S. E. (2012) Advances in Bioinformatics Vol. 2012). Preferably, the specific binding of antibodies to an epitope is mediated by the Fab (fragment, antigen binding) region of the antibody, specific binding of a B-cell is mediated by the Fab region of the antibody comprised by the B-cell receptor and specific binding of a T-cell is mediated by the variable (V) region of the T-cell receptor. T cell epitopes are presented on the surface of an antigen presenting cell, where they are bound to Major Histocompatiblilty (MHC) molecules. There are at least two different classes of MHC molecules termed MHC class I, II respectively. Epitopes presented through the MHC-I pathway elicit a response by cytotoxic T lymphocytes (CD8+ cells), while epitopes presented through the MHC-II pathway elicit a response by T-helper cells (CD4+ cells). T cell epitopes presented by MHC Class I molecules are typically peptides between 8 and 11 amino acids in length and T cell epitopes presented by MHC Class II molecules are typically peptides between 13 and 17 amino acids in length. MHC Class III molecules also present non-peptidic epitopes as glycolipids. Accordingly, the term "T cell epitope" preferably refers to a 8 to 11 or 13 to 17 amino acid long peptide that can be presented by either a MHC Class I or MHC Class II molecule. Epitopes usually consist of chemically active surface groupings of amino acids, which may or may not carry sugar side chains and usually have specific three-dimensional structural characteristics, as well as specific charge characteristics. Conformational and non-conformational epitopes are distinguished in that the binding to the former but not the latter is lost in the presence of denaturing solvents.

The term "cancer specific antigen" is used in the context of the present invention to refer to a protein that is specifically expressed in cancer cells or is more abundant in cancer cells than in healthy cells. Cancer specific antigens include the following types of antigens:

(i) oncofetal (typically only expressed in fetal tissues and in cancerous somatic cells); or (ii) oncoviral (encoded by tumorigenic transforming viruses); or (iii) overexpressed/accumulated (expressed by both normal and neoplastic tissue, with the level of expression highly elevated in neoplasia), e.g. tyrosinase in melanomas or Her-2 receptor in breast cancer; or (iv) cancer-testis (expressed only by cancer cells and adult reproductive tissues such as testis and placenta); or (v) lineage-restricted (expressed largely by a single cancer histotype); or (vi) cancer-specific isoform (alteration of the transcript exon composition).

The term "cancer specific neoantigen" is used in the context of the present invention to refer to an antigen not present in normal/germline cells but which occurs in transformed, in particular cancerous cells. A cancer specific neoantigen may comprise one or more, e.g. 2, 3, 4, 5 or more neoepitopes. It is preferred that the length of each cancer specific neoantigen included in the polypeptide of the present invention is selected in such to ascertain that they there is a low likelihood of comprising epitopes that occur in normal/germline cells. Typically, this can be ascertained in that the cancer specific neoantigen comprises 12 or less amino acids C-terminally and/or N-terminally of the amino acid change(s) that created the neoepitope.

The cancer specific neoantigen is preferably generated by a mutation occurring at level of DNA and wherein the mutated protein can comprise a) one or more single aa changes caused by a non-synonymous SNV point mutation; and/or b) a non-wildtype amino acid sequence caused by insertions/deletions resulting in frame shifted peptide; and/or c) a non-wildtype amino acid sequence caused by alteration of exon boundaries or by mutations generating intron retention; and/or d) a mutated cancer protein generated by a gene fusion event.

A neoantigen that is the result of one or more single amino acid changes caused by a genomic point mutation non-synonymous SNV is referred to in the context of the present invention as a single amino acid mutant peptide.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. Examples of polynucleotides are DNA and RNA.

An "isolated polynucleotide" is DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature.

The term "expression cassette" is used in the context of the present invention to refer to a polynucleotide which comprises at least one nucleic acid sequence that is to be expressed, e.g. a nucleic acid encoding a string of cancer specific neoantigens fused to invariant chain of the present invention or fragments thereof, operably linked to transcription and/or translation control sequences. Preferably, an expression cassette includes cis-regulating elements for efficient expression of a given gene, such as promoter, initiation-site and/or polyadenylation-site. Preferably, an expression cassette contains all the additional elements required for the expression of the polynucleotide in the cell of a patient. A typical expression cassette thus contains a promoter operatively linked to the polynucleotide sequence to be expressed and signals required for efficient polyadenylation of the transcript, ribosome binding sites, and translation termination. Additional elements of the cassette may include, for example enhancers. An expression cassette preferably also contains a transcription termination region downstream of the structural gene to provide for efficient termination. The termination region may be obtained from the same gene as the promoter sequence or may be obtained from a different gene.

The term "operably linked" as used in the context of the present invention refers to an arrangement of elements, wherein the components so described are configured so as to perform their usual function. A polynucleotide is "operably linked" when it is placed into a functional relationship with another nucleic acid sequence. For example, a promoter is operably linked to one or more transgenes, if it affects the transcription of the one or more transgenes. Further, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "vector" or "expression vector" are used interchangeably and refer to a polynucleotide, a polynucleotide within some type of envelope, e.g. a viral coat or a liposome, or a polynucleotide complexed with proteins capable of being introduced or of introducing the polynucleotide of the present invention or into a cell, preferably a mammalian cell. Examples of vectors include but are not limited to plasmids, cosmids, phages, liposomes, viruses or artificial chromosomes. In particular, a vector is used to transport the promoter and the polynucleotide of the invention into a suitable host cell. Expression vectors may contain "replicon" polynucleotide sequences that facilitate the autonomous replication of the expression vector in a host cell. Once in the host cell, the expression vector may replicate independently of or coincidental with the host chromosomal DNA, and several copies of the vector and its inserted DNA can be generated. In case that replication incompetent expression vectors are used—which is often the case for safety reasons—the vector may not replicate but merely direct expression of the polynucleotide. Depending on the type of expression vector the expression vector may be lost from the cell, i.e. only transiently expresses the neoantigens encoded by the polynucleotide or may be stable in the cell. Expression vectors typically contain expression cassettes, i.e. the necessary elements that permit transcription of the polynucleotide into an mRNA molecule. If the polynucleotide is RNA transcription is not necessary and, thus the RNA molecules only require translation control elements The term "T cell enhancer amino acid sequence" refers to a polypeptide sequences that when fused to an antigenic sequence increases the induction of T cells in the context of a genetic vaccination.

The terms "preparation" and "composition" as used in the context of the present invention are intended to include the formulation of the active compound, e.g. the Great Apes Adenovirus vector of the present invention with a carrier and/or excipient.

"Pharmaceutically acceptable" as used in the context of the present invention means approved by a regulatory agency of the Federal or a state government or listed in the U.S. Pharmacopeia or other generally recognized pharmacopeia for use in animals, and more particularly in humans.

The term "carrier", as used herein, refers to a pharmacologically inactive substance such as but not limited to a diluent, excipient, surfactants, stabilizers, physiological buffer solutions or vehicles with which the therapeutically active ingredient is administered. Such pharmaceutical carriers can be liquid or solid. Liquid carrier include but are not limited to sterile liquids, such as saline solutions in water and oils, including but not limited to those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like.

"Surfactants" include anionic, cationic, and non-ionic surfactants such as but not limited to sodium deoxycholate, sodium dodecylsulfate, Triton X-100, and polysorbates such as polysorbate 20, polysorbate 40, polysorbate 60, polysorbate 65 and polysorbate 80.

"Stabilizers" include but are not limited to mannitol, sucrose, trehalose, albumin, as well as protease and/or nuclease antagonists.

"Physiological buffer solution" that may be used in the context of the present invention include but are not limited to sodium chloride solution, demineralized water, as well as suitable organic or inorganic buffer solutions such as but not limited to phosphate buffer, citrate buffer, tris buffer (tris (hydroxymethyl)aminomethane), HEPES buffer ([4 (2 hydroxyethyl)piperazino]ethanesulphonic acid) or MOPS buffer (3 morpholino-1 propanesulphonic acid). The choice of the respective buffer in general depends on the desired buffer molarity. Phosphate buffer are suitable, for example, for injection and infusion solutions.

An "effective amount" or "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

As used herein, "treat", "treating", "treatment" or "therapy" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that has previously had the disorder(s); and (e) limiting or preventing recurrence of symptoms in individuals that were previously symptomatic for the disorder(s).

EMBODIMENTS

In the following different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect of the invention the invention relates to a polypeptide comprising:

(a) a fragment of an invariant chain (INV) of a Teleostei comprising or consisting of between 16 to 27 contiguous amino acids of the membrane proximal domain (MPD) of an INV of the Teleostei, wherein the fragment has T cell response enhancer activity and the MPD is characterized by an amino acid sequence selected from:

(i) NQRX$_1$DIKSLEEQX$_2$SX$_3$LX$_4$X$_5$X$_6$X$_7$TX$_8$GRSX$_9$X$_{10}$ (SEQ ID NO: 001)

wherein

X$_1$ is G or N, X$_2$ is H or N, X$_3$ is G or N, X$_4$ is N or Q, X$_5$ is E or A, X$_6$ is Q or E, X$_7$ is L or M, X$_8$ is K or R, X$_9$ is A or V and X$_{10}$ is S or A;

and wherein the fragment is preferably at least 60% identical to SEQ ID NO: 3 [MPD of PO]; or (ii) DQKQQIQZ$_1$LQZ$_2$Z$_3$NQRZ$_4$EKQZ$_5$Z$_6$Z$_7$RZ$_8$RZ$_9$S (SEQ ID NO: 8)

wherein

Z$_1$ is G or D, Z$_2$ is T or A, Z$_3$ is T or S, Z$_4$ is L or M, Z$_5$ is M or V, Z$_6$ is G or S, Z$_7$ is Q or L, Z$_8$ is P or S, and Z$_9$ is E or V;

and wherein the fragment is preferably at least 60% identical to SEQ ID NO: 10 [MPD of BP];

and optionally one or more antigens and/or one or more antigenic fragments thereof;

or (b) a full length Teleostei INV selected from SEQ ID NO: 2, 5, 9 or 12, or variants thereof, which has T cell response enhancer activity, wherein the amino acid sequence of the MPD of the variant is at least 60% identical to SEQ ID NO: 3 [MPD of PO] or 10 [MPD of BP] and one or more antigens and/or one or more antigenic fragments thereof.

Generally it is desired that the fragment of an INV is as short as possible while retaining its T cell antigen stimulatory effect. Preferably, the fragment comprises, more preferably consists of 16 to 27, 17 to 26, 18 to 25, 19 to 24, 20 to 23, 21 to 22 continuous amino acids of the MPD of an INV, preferably of the MPD according to SEQ ID NO: 3 [MPD of PO] or 10 [MPD of BP].

A preferred minimal fragment according to alternative (i) of the first aspect of the invention is of the amino acid sequence:

DIKSLEEQX$_2$SX$_3$LX$_4$X$_5$X$_6$X$_7$(SEQ ID NO: 28) with the above indicated meaning for X$_2$ to X$_7$.

A more preferred minimal fragment according to alternative (i) of the first aspect of the invention is of the amino acid sequence DIKSLEEQHSGLNEQL (SEQ ID NO: 4) or DIKSLEEQNSNLQAEM (SEQ ID NO: 7), with the most preferred minimal fragment being of the amino acid sequence DIKSLEEQHSGLNEQL (SEQ ID NO: 4).

A preferred minimal fragment according to alternative (ii) of the first aspect of the invention is of the amino acid sequence:

QIQZ$_1$LQZ$_2$Z$_3$NQRZ$_4$EKQZ$_5$ (SEQ ID NO: 29) with the above indicated meaning for Z$_1$ to Z$_5$.

A more preferred minimal fragment according to alternative (ii) of the first aspect of the invention is of the amino acid sequence QIQGLQTSNQRLEKQM (SEQ ID NO: 11) or QIQDLQATNQRMEKQV (SEQ ID NO: 14), with the most preferred minimal fragment being of the amino acid sequence QIQGLQTSNQRLEKQM (SEQ ID NO: 11).

While the fragment of the INV can comprise additional sequences N- and/or C-terminally of the MPD, it is preferred that no such sequences are comprised in the fragment and, thus, it is preferred that the fragment consists of the respective continuous stretch of amino acids of the MPD.

If the fragment of the INV comprises additional sequences N- and/or C-terminally of the MPD, it is preferred that the fragment comprises the entire MPD, i.e. 27 amino acids. It is preferred that the fragment does not comprise the TMD but comprises additional C-terminal amino acids of the INV. Preferably, these C-terminal amino acids are immediately consecutive to the MPD.

The sequence of the MPD is preferably based on the MPD sequence of *Paralichthys olivaceus* (PO) according to SEQ ID NO: 003 or *Boleophthalmus pectinirostris* (BP) according to SEQ ID NO: 010. Preferably, the fragment comprises or consists of 16 to 27 amino acids of the MPD, wherein the MPD is at least 60%, more preferably at least 70%, more preferably at least 75%, more preferably at least 80%, more preferably at least 90% identical to SEQ ID NO: 3 or SEQ ID NO: 010.

The fragment may comprise additional N- and/or C-terminal amino acid sequences of an INV. Thus, it is preferred that the overall length of the fragment of the INV is between 16 to 80, 17 to 72, 18 to 55, 19 to 50, 20 to 45, 21, to 40, 22 to 35, 23 to 30 contiguous amino acids.

In a preferred embodiment of the polypeptide of the first aspect of the invention the polypeptide is comprising a fragment of an invariant chain (INV) of a Teleostei comprising or consisting of between 16 to 27 contiguous amino acids of the membrane proximal domain (MPD) of an INV of the Teleostei, wherein the fragment has T cell response enhancer activity and the MPD is characterized by the amino acid sequence DIKSLEEQX$_2$SX$_3$LX$_4$X$_5$X$_6$X$_7$(SEQ ID NO: 28) wherein X$_2$ is H or N, X$_3$ is G or N, X$_4$ is N or Q, X$_5$ is E or A, X$_6$ is Q or E and X$_7$ is L or M, and wherein the fragment is preferably at least 60% identical to SEQ ID NO: 003 and optionally wherein the polypeptide is comprising one or more antigens and/or one or more antigenic fragments thereof.

In a preferred embodiment of the polypeptide of the first aspect of the invention the polypeptide is comprising a fragment of an invariant chain (INV) of a Teleostei comprising or consisting of between 16 to 27 contiguous amino acids of the membrane proximal domain (MPD) of an INV of the Teleostei, wherein the fragment has T cell response enhancer activity and the MPD is characterized by the amino acid sequence QIQZ$_1$LQZ$_2$Z$_3$NQRZ$_4$EKQZ$_5$ (SEQ ID NO: 29) wherein Z$_1$ is G or D, Z$_2$ is T or A, Z$_3$ is T or S, Z$_4$ is L or M, Z$_5$ is M or V and wherein the fragment is preferably at least 60% identical to SEQ ID NO: 10 and optionally wherein the polypeptide is comprising one or more antigens and/or one or more antigenic fragments thereof.

In a preferred embodiment of the polypeptide of the first aspect of the invention the amino acid sequence of:

(a) the MPD according to alternative (a) (i) of claim 1 is any one of SEQ ID NOs: 3 [MPD PO] and 6 [MPD Z1];

(b) the MPD according to alternative (a) (ii) of claim 1 is any one of SEQ ID NOs: 10 [MPD BP] and 13 [MPD Z2]; and/or (c) the Teleostei invariant chain according to alternative (b) of claim 1 is any one of SEQ ID NOs: 2 and 9.

If the fragment consists of 16 to 27 amino acids of the MPD of an INV, preferred fragments have a length of 16 to 27, 17 to 26, 18 to 25, 19 to 24, 20 to 23, 21 to 22 continuous amino acids of the MPD of the INV according to SEQ ID NO: 3, 6, 10 and 13.

In each case outlined above the fragment or variant has T cell response enhancer activity. T cell response enhancer activity can be measured as known in the art or as set out in the attached experiments. It is preferred that the T cell response enhancer activity is at least 50%, preferably at least 80% of the T cell response enhancer activity of the INV fragment according to SEQ ID NO: 004, when coupled to the same antigen or string of antigens.

In a preferred embodiment of the polypeptide of the first aspect of the invention the fragment consists of at least 16 to 27 N-terminal amino acids of the MPD and 1 to 26 consecutive amino acids of the transmembrane domain (TMD) of an INV of a Teleostei immediately N-terminal of the MPD, wherein the TMD of the INV of the Teleostei is preferably characterized by the following amino acid sequence AB$_1$KB$_2$B$_3$GB$_4$TB$_5$LB$_6$CB$_7$LB$_8$B$_9$B$_{10}$QB$_{11}$B$_{12}$B$_{13}$B$_{14}$YB$_{15}$B$_{16}$B$_{17}$ (SEQ ID NO: 15)

wherein

B$_1$ is V, L or Y, B$_2$ is V or I, B$_3$ is V or A, B$_4$ is L, I or F, B$_5$ is V, T or L, B$_6$ is A or V, B$_7$ is V or L, B$_8$ is V or I, B$_9$ is M, S or A, B$_{10}$ is S, A or G, B$_{11}$ is A or V, B$_{12}$ is M or F, B$_{13}$ is I or T, B$_{14}$ is I or A, B$_{15}$ is F or M, B$_{16}$ is L, M or V, B$_{17}$ is V, F or L.

If the fragment comprises additional N- and/or C-terminal amino acid sequences of an INV, it is preferred that the overall length of the fragment of the INV is between 28 to 72, 30 to 65, or 35 to 46 contiguous amino acids.

It has been surprisingly found by the present inventors that a strong T cell response to two or more antigens, preferably neoantigens, can be induced by fusing the INV fragment of alternative (a) of the first aspect of the invention or the INV of alternative (b) of the first aspect of the invention to two or more antigens and/or antigenic fragments thereof. This allows the simultaneous induction of a T cell response against multiple antigens. Thus, regarding both alternative (a) of the first aspect of the invention and alternative (b) of the first aspect of the invention it is preferred that the polypeptide comprises multiple antigens and/or or antigenic fragments thereof. For example, it is preferred that the polypeptide comprises at least 5 different antigens and/or or antigenic fragments thereof, more preferably at least 20 different antigens and/or or antigenic fragments thereof, even more preferably at least 50 different antigens and/or or antigenic fragments thereof, even more preferably at least 100 different antigens and/or or antigenic fragments thereof, even more preferably at least 200 different antigens and/or or antigenic fragments thereof and even more preferably at least 300 different antigens and/or or antigenic fragments thereof.

To accommodate the maximum number of different antigens within one polypeptide it is particularly preferred that the polypeptide comprises antigenic fragments of the antigens.

The antigens are chosen depending on the respective therapeutic application. If the therapeutic or prophylactic vaccination against a proliferative disease is desired the antigen is selected from a cancer-specific antigen or a cancer specific neoantigen. As set out above in particular in the context of cancer vaccination it is preferred that the polypeptide of the first aspect comprises two or more different antigens. It is preferred that the polypeptide comprises at least 5 different cancer specific antigens or antigenic fragments thereof, more preferably at least 20 different cancer specific antigens or antigenic fragments thereof, even more preferably at least 50 different cancer specific antigens or antigenic fragments thereof, even more preferably at least 100 different cancer specific antigens or antigenic fragments thereof, even more preferably at least 200 different cancer specific antigens or antigenic fragments thereof and even more preferably at least 300 different cancer specific antigens or antigenic fragments thereof. Alternatively, it is preferred that the polypeptide comprises at least 5 different cancer specific neoantigens or antigenic fragments thereof, more preferably at least 20 different cancer specific neoantigens or antigenic fragments thereof, even more preferably at least 50 different cancer specific neoantigens or antigenic fragments thereof, even more preferably at least 100 different cancer specific neoantigens or antigenic fragments thereof, even more preferably at least 200 different cancer specific neoantigens or antigenic fragments thereof and even more preferably at least 300 different cancer specific neoantigens or antigenic fragments thereof. Alternatively, it is preferred that the polypeptide comprises at least 5 different cancer specific antigens or neoantigens or antigenic fragments thereof, more preferably at least 20 different cancer specific antigens or neoantigens or antigenic fragments thereof, even more preferably at least 50 different cancer specific antigens or neoantigens or antigenic fragments thereof, even more preferably at least 100 different cancer specific antigens or neoantigens or antigenic fragments thereof, even more preferably at least 200 different cancer specific antigens or neoantigens or antigenic fragments thereof and even more preferably at least 300 different cancer specific antigens or neoantigens or antigenic fragments thereof.

Alternatively, the antigen is a viral protein or an antigenic fragment thereof, a bacterial protein or an antigenic fragment thereof or a fungal protein or an antigenic fragment thereof.

Generally, the prophylactic or therapeutic vaccination against viral, bacterial or fungal infection does not require as many different antigens to be effective as the vaccination in the therapy of proliferative diseases. Nevertheless, there are some viruses like, e.g. HIV that have a large epitope diversity, in particular in the coat proteins. To elicit a broad immune response multiple antigens can be included. It is, thus preferred that the polypeptide comprises at least 5 different viral antigens or an antigenic fragment thereof, more preferably at least 20 different viral antigens or an antigenic fragment thereof, even more preferably at least 50 different viral antigens or an antigenic fragment thereof, even more preferably at least 100 different viral antigens or an antigenic fragment thereof, even more preferably at least 200 different viral antigens or an antigenic fragment thereof and even more preferably at least 300 different viral antigens or an antigenic fragment thereof. The antigens may be chosen from different strains of the same virus and/or from different viral species. In the latter case the vaccine allows immunization against a variety of different viral species.

Alternatively, it is preferred that the polypeptide comprises at least 5 different bacterial antigens or an antigenic fragment thereof, more preferably at least 20 different bacterial antigens or an antigenic fragment thereof, even more preferably at least 50 different bacterial antigens or an antigenic fragment thereof, even more preferably at least 100 different bacterial antigens or an antigenic fragment thereof, even more preferably at least 200 different bacterial antigens or an antigenic fragment thereof and even more preferably at least 300 different bacterial antigens or an antigenic fragment thereof.

Alternatively, it is preferred that the polypeptide comprises at least 5 different fungal antigens or an antigenic fragment thereof, more preferably at least 20 different fungal antigens or an antigenic fragment thereof, even more preferably at least 50 different fungal antigens or an antigenic fragment thereof, even more preferably at least 100 different fungal antigens or an antigenic fragment thereof, even more preferably at least 200 different fungal antigens or an antigenic fragment thereof and even more preferably at least 300 different fungal antigens or an antigenic fragment thereof.

In all of above embodiments it is preferred that the antigens are T cell antigens. T cell antigens are those that are presented by MHC and elicit a T cell response.

Preferably, the antigen or each of the antigens or an antigenic fragments thereof has (have) a length between 8 to 100 amino acids, more preferably 8 to 50 and more preferably 8 to 30 amino acids.

In a preferred embodiment of the polypeptide of the first aspect of the invention the one or more antigens and/or one or more antigenic fragments thereof are located C-terminally of the fragment of the INV according to alternative (a) of the first aspect of the invention or the full length INV according to alternative (b) of the first aspect of the invention. It is particularly preferred that the antigens and/or antigenic fragments thereof are immediately C-terminally to the INV according to alternative (a) or (b) of the first aspect of the invention.

It is preferred that the polypeptides of the invention are produced inside cells of the patient to be vaccinated. The intracellular expression is a prerequisite for MHC presentation and, thus stimulation of a T cell response. Accordingly, in a second aspect the present invention relates to a polynucleotide encoding the polypeptide according to the first aspect of the present invention. Preferably, the polynucleotide is a DNA or RNA. RNA is preferably used to directly elicit translation of the encoded polypeptide. DNA encoding the polypeptide of the first aspect is typically inserted into expression cassettes, which direct transcription of mRNA encoding the polypeptides of the invention. However, the polynucleotide may also be RNA if the polynucleotide is comprised in a vector and the vector is a RNA virus. A preferred RNA for direct application is a self-amplifying RNA (SAM). Most preferably the polynucleotide is DNA.

In a third aspect the present invention relates to a vector comprising the polynucleotide according to the second aspect of the invention. Preferably the polynucleotide of the present invention is operably linked to an expression control sequence.

Two or more vectors are used if the number of different antigens or antigenic fragments thereof to be delivered to a patient is so large that a polynucleotide encoding the fusion polypeptide of the INV and all antigens or antigenic fragments thereof cannot be accommodated in the chosen vector. Accordingly, in a fourth aspect the present invention relates to a collection of two or more different vectors, wherein the different vectors each comprise a polynucleotide according to the second aspect of the present invention encoding a different polypeptide according to the first aspect of the present invention.

The vector of the third aspect or the collection of vectors of the fourth aspect, wherein the vector in each case is independently selected from the group consisting of a plasmid; a cosmid; a liposomal particle, a viral vector or a virus like particle; preferably an alphavirus vector, a venezuelan equine encephalitis (VEE) virus vector, a sindbis (SIN) virus vector, a semliki forest virus (SFV) virus vector, a simian or human cytomegalovirus (CMV) vector, a Lymphocyte choriomeningitis virus (LCMV) vector, a retroviral vector, a lentiviral vector, an adenoviral vector, an adeno-associated virus vector a poxvirus vector, a vaccinia virus vector or a modified vaccinia ankara (MVA) vector. It is preferred that a collection of vectors, wherein each member of the collection comprises a polynucleotide encoding a different antigen or fragments thereof and, which is thus typically administered simultaneously uses the same vector type, e.g. an adenoviral derived vector.

The most preferred vectors are adenoviral vectors, in particular adenoviral vectors derived from human or non-human great apes. Preferred great apes from which the adenoviruses are derived are Chimpanzee (Pan), Gorilla (Gorilla) and orangutans (Pongo), preferably Bonobo (Pan paniscus) and common Chimpanzee (Pan troglodytes). Typically, naturally occurring non-human great ape adenoviruses are isolated from stool samples of the respective great ape. The most preferred vectors are non-replicating adenoviral vectors based on hAd5, hAd11, hAd26, hAd35, hAd49, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd 73, ChAd82, ChAd83, ChAd146, ChAd147, PanAd1, PanAd2, and PanAd3 vectors or replication-competent Ad4 and Ad7 vectors. The human adenoviruses hAd4, hAd5, hAd7, hAd11, hAd26, hAd35 and hAd49 are well known in the art. Vectors based on naturally occurring ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in detail in WO 2005/071093. Vectors based on naturally occurring PanAd1, PanAd2, PanAd3, ChAd55, ChAd73, ChAd83, ChAd146, and ChAd147 are described in detail in WO 2010/086189.

In a fifth aspect the present invention relates to a pharmaceutical composition comprising the polypeptide of the first aspect of the present invention, a polynucleotide of the second aspect of the present invention or a vector of the third aspect of the present invention or collection of vectors of the fourth aspect of the invention and a pharmaceutically acceptable excipient and optionally one or more adjuvants.

The present inventors have found that the administration of at least one immunomodulator, for example a modulator of a checkpoint molecule (MCM), further improves the strength of the T cell response to the antigen or a fragment thereof. Thus, in a preferred embodiment of the fifth aspect the pharmaceutical composition comprises at least one immunomodulator, for example a MCM, or at least one polynucleotide encoding the immunomodulator, for example a MCM, or a vector or liposomal particle comprising the polynucleotide encoding the immunomodulator, for example a MCM.

In a sixth aspect the present invention relates to a kit of parts comprising the pharmaceutical composition of the fifth aspect of the present invention and separately packaged at least one immunomodulator, for example a MCM, or at least one polynucleotide encoding the immunomodulator, for example a MCM, or a vector comprising the polynucleotide encoding the the immunomodulator, for example a MCM.

In a preferred embodiment of the fifth aspect or sixth aspect the immunomodulator is a MCM and is selected from the group consisting of:

(a) an agonist of a tumor necrosis factor (TNF) receptor superfamily member, preferably of CD27 (e.g. Varlilumab), CD40 (e.g. CP-870,893), OX40 (e.g. INCAGN01949 or MEDI0562), GITR (e.g. MEDI1873) or CD137 (e.g. Utomilumab);

(b) an antagonist of PD-1 (e.g. pembrolizumab or nivolumab), CD274 (atezolizumab or Durvalumab), A2AR (e.g. Preladenant), B7-H3 (e.g. MGA271), B7-H4, BTLA, CTLA-4 (e.g. Tremelimumab or AGEN1884), IDO, KIR, LAG3, TIM-3 (e.g. CA-327 or RMT3-23), or VISTA (e.g. CA-170) or an antagonist of a B7-CD28 superfamily member, preferably of CD28 or ICOS or an antagonist of a ligand thereof.

Other preferred immunomodulators are cytokines that act as T cell growth factors, in particular IL-2, IL-12, or IL-15.

In a seventh aspect the present invention relates to polypeptide according to the first aspect of the invention, a polynucleotide according to the second aspect of the invention, or a vector or a collection of vectors according to third or fourth aspect of the invention, or a pharmaceutical composition according to the fifth aspect of the invention or kits comprising such pharmaceutical compositions according to the sixth aspect of the invention or use in preventing or treating a proliferative disease, preferably cancer, viral disease, fungal disease or bacterial disease.

In a preferred embodiment the polypeptide according to the first aspect of the invention, the polynucleotide according to the second aspect of the invention, or the vector or a collection of vectors according to third or fourth aspect of the invention, or the pharmaceutical composition or kits comprising such pharmaceutical compositions according fifth aspect of the invention, wherein the cancer is selected from the group consisting of malignant neoplasms of lip, oral cavity, pharynx, a digestive organ, respiratory organ, intrathoracic organ, bone, articular cartilage, skin, mesothelial tissue, soft tissue, breast, female genital organs, male genital organs, urinary tract, brain and other parts of central nervous system, thyroid gland, endocrine glands, lymphoid tissue, and haematopoietic tissue.

In a preferred embodiment the polypeptide according to the first aspect of the invention, the polynucleotide according to the second aspect of the invention, or the vector or a collection of vectors according to third or fourth aspect of the invention, or the pharmaceutical composition or kits comprising such pharmaceutical compositions according fifth aspect of the invention, wherein at least one immuno-modulator, for example a MCM, or at least one polynucle-otide encoding the immunomodulator, for example a MCM, or a vector or liposomal particle comprising the polynucle-otide encoding the immunomodulator, for example a MCM, is administered prior to, concomitantly with or subsequently to the administration of the polypeptide according to the first aspect of the invention, the polynucleotide according to the second aspect of the invention, or the vector or a collection of vectors according to third or fourth aspect of the inven-tion, or the pharmaceutical composition or kits comprising such pharmaceutical compositions according fifth aspect of the invention.

In a preferred embodiment of the seventh aspect of the invention the administration of the modulator of a check-point molecule is initiated before initiation of administration of the vaccine, or wherein administration of the checkpoint inhibitor is initiated after initiation of administration of the vaccine, or wherein administration of the checkpoint inhibi-tor is initiated simultaneously with the initiation of admin-istration of the vaccine.

In a preferred embodiment of the seventh aspect of the invention the vaccination regimen is a heterologous prime boost with two different viral vectors. Preferred combina-tions are Great Apes derived adenoviral vector for priming and a poxvirus vector, a vaccinia virus vector or a modified vaccinia ankara (MVA) vector for boosting being. Prefer-ably these are administered sequentially with an interval of at least 1 week, preferably of 6 weeks.

In an eight aspect the present invention relates to a polypeptide according to the first aspect of the invention, a polynucleotide according to the second aspect of the inven-tion, or a vector or a collection of vectors according to third or fourth aspect of the invention for use as a medicament.

EXAMPLES

Teleost Invariant Chains and Fragments Thereof Turn Non-Immunogenic Cancer Antigens into Immunogenic Antigens Immunogenicity of Great Ape Adenovectors encoding for five cancer neoantigens (Table 1, SEQ ID NO: 16 to 20) derived from the CT26 murine tumor cell line was evaluated in BalBC inbred mice. Vector GAd-penta, encoding only the five cancer neoantigens joined head to tail (penta) plus an initial Met and a C-terminal HA tag (SEQ ID NO: 21), was found not to be immunogenic unless full length Teleostei Invariant chain sequences (BP_INV FL [SEQ ID NO: 9] or PO_INV FL [SEQ ID NO: 2]) or fragments thereof (frag-ment BP_FRAG_A [SEQ ID NO: 10] or BP_FRAG_B [SEQ ID NO: 11] or PO_FRAG_A [SEQ ID NO: 3] or PO_FRAG_B [SEQ ID NO: 4]) were added to the N-ter-minus of the penta antigen (SEQ ID NO: 22 to 27). Mice were immunized by a single intramuscular immunization of GAds at doses of $10^8$ viral particles (vp). Splenocytes were collected two weeks after immunization and tested by IFN-γ ELISpot by stimulating T cells in the presence of synthetic peptides corresponding to the amino acid sequence of the five neoantigens. Negative-control cultures included cells stimulated with culture medium alone but containing the solvent dimethyl sulfoxide (DMSO) used for the preparation of the peptides. Immune responses (number of T cells producing IFN-γ per million splenocytes) are shown in FIG. 1. Responses were considered positive if (i) at least 20 specific spots/million splenocytes were detected; (ii) the number of spots seen in positive wells exceeded three times the number detected in the mock control wells (DMSO). As shown in FIG. 1, linkage of BP_INV FL or PO_INV FL or fragments FRAG_A or FRAG_B thereof to the N-terminus of the penta antigen converted the non-immunogenic vac-cine construct Gad-Penta into highly immunogenic con-structs with 100% of the vaccinated animals showing posi-tive immunological responses.

TABLE 1

Penta antigen: Composition of the penta antigen. CT26 neoantigens are present in the assembled penta antigen in the order shown. The mutated amino acid is indicated in bold and underlined for each neoantigen

| SEQ ID NO | Neoantigen | Gene |
|---|---|---|
| 16 | LLPFYPPDEALEIGLELNSSALPPT | SLC4A3 |
| 17 | ILPQAPSGPSYATYLQPAQAQMLTP | E2F8 |
| 18 | KPLRRNNSYTSYIMAICGMPLDSFR | SLC20A1 |
| 19 | VIQTSKYYMRDVIAIESAWLLELAP | DHX35 |
| 020 | HIHRAGGLFVADAIQVGFGRIGKHF | AGXT2L2 |

Materials and Methods

Mouse Immunization 6-week-old female BalBC mice were purchased from Envigo laboratories. Mice were all vaccinated intramuscu-larly (in the quadriceps) by injecting 50 μl of viral vectors per side (total volume of 100 μl) at the doses of $10^8$ vp.

IFNγ ELISpot

IFNγ-producing T cells were evaluated by an ELISPOT assay 2 weeks post vaccination. MSIP S4510 plates (Mil-lipore) were coated with 10 μg/ml of anti-mouse IFNγ (U-CyTech Utrecht, The Netherlands) overnight at 4° C. After washing and blocking, mouse splenocytes were plated in duplicate at two different densities ($2.5×10^5$ and $5×10^5$ cells/well) and stimulated overnight with a pool of 25mer synthetic peptides corresponding to the antigen vaccine sequence (FIG. 1), at final concentration of 2 μg/ml each peptide. The peptide diluent DMSO (Sigma-Aldrich, Milan, Italy) and ConA (Sigma-Aldrich, Milan, Italy) were used respectively as negative and positive controls. Plates were developed by subsequent incubations with biotinylated anti-mouse IFNγ antibody (U-CyTech Utrecht, The Nether-lands), Streptavidin-Alkaline Phosphatase conjugated (BD Biosciences, NJ) and finally with BCIP/NBT 1-Step solution (Thermo Fisher Scientific, Rockford, IL). Plates were acquired and analyzed by a CTL automated plate reader. The ELISpot response was considered positive when all of the following conditions were met: IFNγ production present in Con-A stimulated wells; at least 20 specific spots/million splenocytes; the number of spots seen in positive wells three times higher than the number detected in the mock control wells (DMSO); and decreased responses with cell dilutions. ELISpot data were expressed as IFNγ spot forming cells (SFC) per million splenocytes.

The invention claimed is:

1. A method for treating or limiting the development of a cancer comprising administering to a subject in need thereof a polynucleotide or a vector comprising said polynucleotide, in an amount effective to limit the development of or treat said cancer, wherein the polynucleotide encodes a polypeptide consisting of a fragment of an invariant chain (INV) of a Teleostei consisting of between 16 to 27 contiguous amino acids of the membrane proximal domain (MPD) of the INV of the Teleostei, wherein the fragment has T cell response enhancer activity and the MPD is characterized by an amino acid sequence selected from SEQ ID NOs: 3, 4, 10, and 11; and one or more cancer-specific antigens or cancer-specific neoantigens and/or one or more antigenic fragments thereof.

2. The method according to claim 1, wherein at least one immunomodulator, or at least one polynucleotide encoding the immunomodulator, or a vector or liposomal particle comprising the polynucleotide encoding the immunomodulator, is administered prior to, concomitantly with or subsequently to the administration of the polynucleotide encoding the polypeptide or the vector comprising said polynucleotide encoding the polypeptide.

3. The method according to claim 1, wherein the cancer is selected from the group consisting of malignant neoplasms of lip, oral cavity, pharynx, a digestive organ, respiratory organ, intrathoracic organ, bone, articular cartilage, skin, mesothelial tissue, soft tissue, breast, female genital organs, male genital organs, urinary tract, brain and other parts of central nervous system, thyroid gland, endocrine glands, lymphoid tissue, and haematopoietic tissue.

4. The method according to claim 1, wherein the amino acid sequence of the MPD is any one of SEQ ID NOs: 3 and 4.

5. The method according to claim 1, wherein the polypeptide comprises at least five different antigens and/or antigenic fragments thereof.

6. A method for treating or limiting the development of a cancer, comprising administering to a subject in need thereof a collection of two or more different vectors in an amount effective to limit the development of or treat said cancer, wherein the different vectors each comprise a polynucleotide encoding a different polypeptide according to claim 1.

7. The method according to claim 6, wherein at least one immunomodulator, or at least one polynucleotide encoding the immunomodulator, or a vector or liposomal particle comprising the polynucleotide encoding the immunomodulator, is administered prior to, concomitantly with or subsequently to the administration of the different vectors.

8. The method according to claim 6, wherein the cancer is selected from the group consisting of malignant neoplasms of lip, oral cavity, pharynx, a digestive organ, respiratory organ, intrathoracic organ, bone, articular cartilage, skin, mesothelial tissue, soft tissue, breast, female genital organs, male genital organs, urinary tract, brain and other parts of central nervous system, thyroid gland, endocrine glands, lymphoid tissue, and haematopoietic tissue.

9. A method for inducing an immune response in a subject comprising administering to the subject a polynucleotide or a vector comprising said polynucleotide, wherein the polynucleotide encodes a polypeptide consisting of a fragment of an invariant chain (INV) of a Teleostei consisting of between 16 to 27 contiguous amino acids of the membrane proximal domain (MPD) of the INV of the Teleostei, wherein the fragment has T cell response enhancer activity and the MPD is characterized by an amino acid sequence selected from SEQ ID NOs: 3, 4, 10, and 11; and one or more cancer-specific antigens or cancer-specific neoantigens and/or one or more antigenic fragments thereof.

* * * * *

SEQUENCE LISTING

<160> NUMBER OF SEQ ID NOS: 30

<210> SEQ ID NO 1
<211> LENGTH: 27
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (4)..(4)
<223> OTHER INFORMATION: Xaa is G or N
<220> FEATURE:
<221> NAME/KEY: MISC_FEATURE
<222> LOCATION: (13)..(13)
<223> OTHER INFORMATION: Xaa is H or N
<220> FEATURE:
<221> NAME/KEY: MISC_FEATURE
<222> LOCATION: (15)..(15)
<223> OTHER INFORMATION: Xaa is G or N
<220> FEATURE:
<221> NAME/KEY: MISC_FEATURE
<222> LOCATION: (17)..(17)
<223> OTHER INFORMATION: Xaa is N or Q
<220> FEATURE:
<221> NAME/KEY: MISC_FEATURE
<222> LOCATION: (18)..(18)
<223> OTHER INFORMATION: Xaa is E or A
<220> FEATURE:
<221> NAME/KEY: MISC_FEATURE
<222> LOCATION: (19)..(19)
<223> OTHER INFORMATION: Xaa is Q or E
<220> FEATURE:
<221> NAME/KEY: MISC_FEATURE
<222> LOCATION: (20)..(20)
<223> OTHER INFORMATION: Xaa is L or M
<220> FEATURE:
<221> NAME/KEY: MISC_FEATURE
<222> LOCATION: (22)..(22)
<223> OTHER INFORMATION: Xaa is K or R
<220> FEATURE:
<221> NAME/KEY: MISC_FEATURE
<222> LOCATION: (26)..(26)
<223> OTHER INFORMATION: Xaa is A or V
<220> FEATURE:
<221> NAME/KEY: MISC_FEATURE
<222> LOCATION: (27)..(27)
<223> OTHER INFORMATION: Xaa is S or A

<400> SEQUENCE: 1

Asn Gln Arg Xaa Asp Ile Lys Ser Leu Glu Glu Gln Xaa Ser Xaa Leu
1               5                   10                  15

Xaa Xaa Xaa Xaa Thr Xaa Gly Arg Ser Xaa Xaa
            20                  25

<210> SEQ ID NO 2
<211> LENGTH: 187
<212> TYPE: PRT
<213> ORGANISM: Paralichthys olivaceus

<400> SEQUENCE: 2

Met Ser Glu Thr Gln Thr Leu Leu Gly Ala Pro Arg Gln Gln Thr Ala
1               5                   10                  15

Val Asp Val Gly Ala Pro Ala Gln Gly Gly Arg Ser Ala Asn Ala Tyr
            20                  25                  30

Lys Val Val Gly Leu Thr Val Leu Ala Cys Val Leu Val Met Ser Gln
        35                  40                  45

Ala Met Ile Ile Tyr Phe Leu Val Asn Gln Arg Gly Asp Ile Lys Ser
    50                  55                  60

Leu Glu Glu Gln His Ser Gly Leu Asn Glu Gln Leu Thr Lys Gly Arg

-continued

```
65                    70                    75                    80
Ser Ala Ser Met Ser Met Gln Leu Pro Ser Ser Phe His Ser Leu Thr
                    85                    90                    95

Phe Asp Glu Lys Ser Ser Thr Arg Ala Pro Glu Glu Thr Gly Pro Pro
                100                   105                   110

Gln Ala Thr Gln Cys Gln Leu Glu Ala Ala Gly Glu Lys Pro Val Gln
                115                   120                   125

Val Pro Gly Leu Arg Pro Asp Cys Asp Glu Arg Gly Leu Tyr Arg Leu
        130                   135                   140

Lys Gln Cys Leu Lys His Arg Cys Trp Cys Val Asn Pro Ala Asn Gly
145                   150                   155                   160

Glu Gln Ile Pro Gly Ser Leu Gly Lys Glu Asp Val Thr Cys Asn Lys
                    165                   170                   175

Gly Val His Ser Val Gly Leu Asp Lys Val Leu
                180                   185

<210> SEQ ID NO 3
<211> LENGTH: 27
<212> TYPE: PRT
<213> ORGANISM: Paralichthys olivaceus

<400> SEQUENCE: 3

Asn Gln Arg Gly Asp Ile Lys Ser Leu Glu Glu Gln His Ser Gly Leu
1               5                   10                  15

Asn Glu Gln Leu Thr Lys Gly Arg Ser Ala Ser
            20                  25

<210> SEQ ID NO 4
<211> LENGTH: 16
<212> TYPE: PRT
<213> ORGANISM: Paralichthys olivaceus

<400> SEQUENCE: 4

Asp Ile Lys Ser Leu Glu Glu Gln His Ser Gly Leu Asn Glu Gln Leu
1               5                   10                  15

<210> SEQ ID NO 5
<211> LENGTH: 196
<212> TYPE: PRT
<213> ORGANISM: Larimichthys crocea

<400> SEQUENCE: 5

Met Ser Asp Pro Glu Thr Pro Asn Gln Pro Leu Leu Gln Ala Ala Thr
1               5                   10                  15

Asn Val Pro Ala Ala Gln Arg Gly Ser Ser Ser Arg Ala Tyr Lys Val
                20                  25                  30

Ala Gly Phe Thr Leu Leu Ala Cys Leu Leu Ile Ala Gly Gln Ala Met
            35                  40                  45

Ile Ala Tyr Phe Leu Leu Asn Gln Arg Asn Asp Ile Lys Ser Leu Glu
        50                  55                  60

Glu Gln Asn Ser Asn Leu Gln Ala Glu Met Thr Arg Gly Arg Ser Val
65                  70                  75                  80

Ala Val Pro Met Arg Thr His Met Ala Met Asn Ala Leu Pro Val Met
                85                  90                  95

Asp Val Ser Met Asp Glu Asp Ser Ser Ile Thr Asp Pro Glu Lys Pro
                100                 105                 110

Ala Pro Arg Gln Val Thr Asp Cys Gln Leu Glu Ala Ala Gly Lys Lys
            115                 120                 125
```

```
Pro Val Gln Val Pro Gly Phe Arg Pro Ser Cys Asp Glu Arg Gly Leu
    130                 135                 140

Tyr Gln Pro Gln Gln Cys Phe Met Thr Gln Cys Trp Cys Val Asn Pro
145                 150                 155                 160

Ala Asn Gly Lys Gln Ile Pro Gly Ser Leu Lys Asn Gly Gln Ala Ser
                165                 170                 175

Cys Arg Ala Ala Val Ile Ala Val Ser Arg Ile Glu Tyr Ile Cys Thr
            180                 185                 190

Asp Val Gln Glu
        195

<210> SEQ ID NO 6
<211> LENGTH: 27
<212> TYPE: PRT
<213> ORGANISM: Larimichthys crocea

<400> SEQUENCE: 6

Asn Gln Arg Asn Asp Ile Lys Ser Leu Glu Glu Gln Asn Ser Asn Leu
1                 5                 10                 15

Gln Ala Glu Met Thr Arg Gly Arg Ser Val Ala
                20                 25

<210> SEQ ID NO 7
<211> LENGTH: 16
<212> TYPE: PRT
<213> ORGANISM: Larimichthys crocea

<400> SEQUENCE: 7

Asp Ile Lys Ser Leu Glu Glu Gln Asn Ser Asn Leu Gln Ala Glu Met
1                 5                 10                 15

<210> SEQ ID NO 8
<211> LENGTH: 27
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (8)..(8)
<223> OTHER INFORMATION: Xaa is G or D
<220> FEATURE:
<221> NAME/KEY: MISC_FEATURE
<222> LOCATION: (11)..(11)
<223> OTHER INFORMATION: Xaa is T or A
<220> FEATURE:
<221> NAME/KEY: MISC_FEATURE
<222> LOCATION: (12)..(12)
<223> OTHER INFORMATION: Xaa is T or S
<220> FEATURE:
<221> NAME/KEY: MISC_FEATURE
<222> LOCATION: (16)..(16)
<223> OTHER INFORMATION: Xaa is L or M
<220> FEATURE:
<221> NAME/KEY: MISC_FEATURE
<222> LOCATION: (20)..(20)
<223> OTHER INFORMATION: Xaa is M or V
<220> FEATURE:
<221> NAME/KEY: MISC_FEATURE
<222> LOCATION: (21)..(21)
<223> OTHER INFORMATION: Xaa is G or S
<220> FEATURE:
<221> NAME/KEY: MISC_FEATURE
<222> LOCATION: (22)..(22)
<223> OTHER INFORMATION: Xaa is Q or L
<220> FEATURE:
<221> NAME/KEY: MISC_FEATURE
<222> LOCATION: (24)..(24)
```

```
<223> OTHER INFORMATION: Xaa is P or S
<220> FEATURE:
<221> NAME/KEY: MISC_FEATURE
<222> LOCATION: (26)..(26)
<223> OTHER INFORMATION: Xaa is E or V

<400> SEQUENCE: 8

Asp Gln Lys Gln Gln Ile Gln Xaa Leu Gln Xaa Xaa Asn Gln Arg Xaa
1               5                   10                  15

Glu Lys Gln Xaa Xaa Xaa Arg Xaa Arg Xaa Ser
            20                  25

<210> SEQ ID NO 9
<211> LENGTH: 197
<212> TYPE: PRT
<213> ORGANISM: Boleophthalmus pectiniros

<400> SEQUENCE: 9

Met Glu His Ala Ser Glu Asp Ala Pro Leu Ala Arg Asp Ser Gly Thr
1               5                   10                  15

Gly Ser Glu Gln Ala Leu Val Val Pro Thr Ala Pro Arg Arg Gly Ser
            20                  25                  30

Asn Ser His Ala Val Lys Ile Ala Gly Ile Thr Thr Leu Val Cys Leu
        35                  40                  45

Leu Val Ser Ala Gln Val Phe Thr Ala Tyr Met Val Phe Asp Gln Lys
        50                  55                  60

Gln Gln Ile Gln Gly Leu Gln Thr Ser Asn Gln Arg Leu Glu Lys Gln
65                  70                  75                  80

Met Gly Gln Arg Pro Arg Glu Ser Leu Lys Lys Ile Val Met Pro Ala
                85                  90                  95

Asn Ser Met Pro Ile Leu Asp Phe Phe Asp Asp Gly Lys Ser Pro Gln
                100                 105                 110

Asn Ser Pro Lys Ala Glu Pro Pro Lys Gln Asp Val Ala Pro Pro Ser
            115                 120                 125

Val Glu Lys Gln Leu Gln Glu Leu Met Lys Val Phe Thr Asp Phe Pro
        130                 135                 140

Gln Met Asn Glu Ser Phe Leu Ala Asn Leu Gln Thr Met Lys Gln Lys
145                 150                 155                 160

Val Ser Glu Thr Asp Trp Lys Ser Phe Glu Ala Trp Met His Tyr Trp
                165                 170                 175

Leu Ile Phe Gln Met Ala Gln Lys Thr Ser Thr Pro Thr Pro Gln Pro
                180                 185                 190

Asp Gly Gly Ser Lys
        195

<210> SEQ ID NO 10
<211> LENGTH: 27
<212> TYPE: PRT
<213> ORGANISM: Boleophthalmus pectiniros

<400> SEQUENCE: 10

Asp Gln Lys Gln Gln Ile Gln Gly Leu Gln Thr Ser Asn Gln Arg Leu
1               5                   10                  15

Glu Lys Gln Met Gly Gln Arg Pro Arg Glu Ser
            20                  25

<210> SEQ ID NO 11
<211> LENGTH: 16
<212> TYPE: PRT
```

-continued

<213> ORGANISM: Boleophthalmus pectiniros

<400> SEQUENCE: 11

Gln Ile Gln Gly Leu Gln Thr Ser Asn Gln Arg Leu Glu Lys Gln Met
1               5                   10                  15

<210> SEQ ID NO 12
<211> LENGTH: 278
<212> TYPE: PRT
<213> ORGANISM: Boleophthalmus pectiniros

<400> SEQUENCE: 12

Met Glu His Ser Ser Glu Glu Ala Pro Leu Ala Ala Asp Ser Arg Ala
1               5                   10                  15

Gly Ser Glu Gln Val Leu Ile Pro Ala Ser Gly Thr Pro Gly Gly Ser
            20                  25                  30

Asn Gly His Ala Leu Lys Ile Ala Gly Ile Thr Thr Leu Val Cys Leu
        35                  40                  45

Leu Val Ser Ala Gln Val Phe Thr Ala Tyr Met Met Phe Asp Gln Lys
        50                  55                  60

Gln Gln Ile Gln Asp Leu Gln Ala Thr Asn Gln Arg Met Glu Lys Gln
65                  70                  75                  80

Val Ser Leu Arg Ser Arg Val Ser Pro Gln Lys Met Val Met Pro Met
                85                  90                  95

Ala Ser Met Pro Leu Leu Asp Phe Ser Asp Asp Ser Asn Ala Pro Asn
            100                 105                 110

Pro Thr Thr Pro Lys Glu Ala Pro Lys Leu Asn Lys Thr Pro Ser Pro
            115                 120                 125

Pro Ser Val Glu Glu Gln Leu Met Asp Leu Met Lys Asp Leu Glu Leu
        130                 135                 140

Pro His Phe Asn Lys Thr Phe Leu Ala Asn Leu Gln Thr Leu Lys Gln
145                 150                 155                 160

Gln Val Asn Glu Thr Ser Trp Lys Ser Leu Glu Ser Trp Leu Arg Tyr
                165                 170                 175

Trp Leu Ile Phe Gln Met Ala Gln Lys Ala Pro Thr Pro Gln Pro Ala
            180                 185                 190

Ser Glu Val Lys Thr Lys Cys Gln Ser Glu Ala Ala Ala Gly Val Ser
            195                 200                 205

Gly Leu Ile Gly Ala Tyr Arg Pro Gln Cys Asp Glu Gln Gly Asn Tyr
        210                 215                 220

Lys Arg Met Gln Cys Trp His Ala Thr Arg Gln Cys Trp Cys Val Asp
225                 230                 235                 240

Glu Ser Gly Thr Pro Ile Asp Gly Ser Asn Thr Gln Gly Arg Pro Asn
                245                 250                 255

Cys Asp Gln Phe Leu Arg Ala Arg Arg Thr Lys Ser Asn Thr Leu Met
            260                 265                 270

Leu Ala Asp Leu Thr Asp
        275

<210> SEQ ID NO 13
<211> LENGTH: 27
<212> TYPE: PRT
<213> ORGANISM: Boleophthalmus pectiniros

<400> SEQUENCE: 13

Asp Gln Lys Gln Gln Ile Gln Asp Leu Gln Ala Thr Asn Gln Arg Met
1               5                   10                  15

-continued

```
Glu Lys Gln Val Ser Leu Arg Ser Arg Val Ser
            20                  25

<210> SEQ ID NO 14
<211> LENGTH: 16
<212> TYPE: PRT
<213> ORGANISM: Boleophthalmus pectiniros

<400> SEQUENCE: 14

Gln Ile Gln Asp Leu Gln Ala Thr Asn Gln Arg Met Glu Lys Gln Val
1               5                   10                  15

<210> SEQ ID NO 15
<211> LENGTH: 26
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (2)..(2)
<223> OTHER INFORMATION: Xaa is V, L or Y
<220> FEATURE:
<221> NAME/KEY: MISC_FEATURE
<222> LOCATION: (4)..(4)
<223> OTHER INFORMATION: Xaa is V or I
<220> FEATURE:
<221> NAME/KEY: MISC_FEATURE
<222> LOCATION: (5)..(5)
<223> OTHER INFORMATION: Xaa is V or A
<220> FEATURE:
<221> NAME/KEY: MISC_FEATURE
<222> LOCATION: (7)..(7)
<223> OTHER INFORMATION: Xaa is L, I or F
<220> FEATURE:
<221> NAME/KEY: MISC_FEATURE
<222> LOCATION: (9)..(9)
<223> OTHER INFORMATION: Xaa is V, T or L
<220> FEATURE:
<221> NAME/KEY: MISC_FEATURE
<222> LOCATION: (11)..(11)
<223> OTHER INFORMATION: Xaa is A or V
<220> FEATURE:
<221> NAME/KEY: MISC_FEATURE
<222> LOCATION: (13)..(13)
<223> OTHER INFORMATION: Xaa is V or L
<220> FEATURE:
<221> NAME/KEY: MISC_FEATURE
<222> LOCATION: (15)..(15)
<223> OTHER INFORMATION: Xaa is V or I
<220> FEATURE:
<221> NAME/KEY: MISC_FEATURE
<222> LOCATION: (16)..(16)
<223> OTHER INFORMATION: Xaa is M, S or A
<220> FEATURE:
<221> NAME/KEY: MISC_FEATURE
<222> LOCATION: (17)..(17)
<223> OTHER INFORMATION: Xaa is S, A or G
<220> FEATURE:
<221> NAME/KEY: MISC_FEATURE
<222> LOCATION: (19)..(19)
<223> OTHER INFORMATION: Xaa is A or V
<220> FEATURE:
<221> NAME/KEY: MISC_FEATURE
<222> LOCATION: (20)..(20)
<223> OTHER INFORMATION: Xaa is M or F
<220> FEATURE:
<221> NAME/KEY: MISC_FEATURE
<222> LOCATION: (21)..(21)
<223> OTHER INFORMATION: Xaa is I or T
<220> FEATURE:
<221> NAME/KEY: MISC_FEATURE
<222> LOCATION: (22)..(22)
<223> OTHER INFORMATION: Xaa is I or A
<220> FEATURE:
```

```
<221> NAME/KEY: MISC_FEATURE
<222> LOCATION: (24)..(24)
<223> OTHER INFORMATION: Xaa is F or M
<220> FEATURE:
<221> NAME/KEY: MISC_FEATURE
<222> LOCATION: (25)..(25)
<223> OTHER INFORMATION: Xaa is L, M or V
<220> FEATURE:
<221> NAME/KEY: MISC_FEATURE
<222> LOCATION: (26)..(26)
<223> OTHER INFORMATION: Xaa is V, F or L

<400> SEQUENCE: 15

Ala Xaa Lys Xaa Xaa Gly Xaa Thr Xaa Leu Xaa Cys Xaa Leu Xaa Xaa
1               5                   10                  15

Xaa Gln Xaa Xaa Xaa Xaa Tyr Xaa Xaa Xaa
            20                  25

<210> SEQ ID NO 16
<211> LENGTH: 25
<212> TYPE: PRT
<213> ORGANISM: Mus musculus

<400> SEQUENCE: 16

Leu Leu Pro Phe Tyr Pro Pro Asp Glu Ala Leu Glu Ile Gly Leu Glu
1               5                   10                  15

Leu Asn Ser Ser Ala Leu Pro Pro Thr
            20                  25

<210> SEQ ID NO 17
<211> LENGTH: 25
<212> TYPE: PRT
<213> ORGANISM: Mus musculus

<400> SEQUENCE: 17

Ile Leu Pro Gln Ala Pro Ser Gly Pro Ser Tyr Ala Thr Tyr Leu Gln
1               5                   10                  15

Pro Ala Gln Ala Gln Met Leu Thr Pro
            20                  25

<210> SEQ ID NO 18
<211> LENGTH: 25
<212> TYPE: PRT
<213> ORGANISM: Mus musculus

<400> SEQUENCE: 18

Lys Pro Leu Arg Arg Asn Asn Ser Tyr Thr Ser Tyr Ile Met Ala Ile
1               5                   10                  15

Cys Gly Met Pro Leu Asp Ser Phe Arg
            20                  25

<210> SEQ ID NO 19
<211> LENGTH: 25
<212> TYPE: PRT
<213> ORGANISM: Mus musculus

<400> SEQUENCE: 19

Val Ile Gln Thr Ser Lys Tyr Tyr Met Arg Asp Val Ile Ala Ile Glu
1               5                   10                  15

Ser Ala Trp Leu Leu Glu Leu Ala Pro
            20                  25

<210> SEQ ID NO 20
<211> LENGTH: 25
```

```
<212> TYPE: PRT
<213> ORGANISM: Mus musculus

<400> SEQUENCE: 20

His Ile His Arg Ala Gly Gly Leu Phe Val Ala Asp Ala Ile Gln Val
1               5                   10                  15

Gly Phe Gly Arg Ile Gly Lys His Phe
            20                  25

<210> SEQ ID NO 21
<211> LENGTH: 137
<212> TYPE: PRT
<213> ORGANISM: Artificial Sequence
<220> FEATURE:
<223> OTHER INFORMATION: Penta antigen with N-terminal met and
      C-terminal HA tag

<400> SEQUENCE: 21

Met Leu Leu Pro Phe Tyr Pro Pro Asp Glu Ala Leu Glu Ile Gly Leu
1               5                   10                  15

Glu Leu Asn Ser Ser Ala Leu Pro Pro Thr Ile Leu Pro Gln Ala Pro
            20                  25                  30

Ser Gly Pro Ser Tyr Ala Thr Tyr Leu Gln Pro Ala Gln Ala Gln Met
        35                  40                  45

Leu Thr Pro Lys Pro Leu Arg Arg Asn Asn Ser Tyr Thr Ser Tyr Ile
    50                  55                  60

Met Ala Ile Cys Gly Met Pro Leu Asp Ser Phe Arg Val Ile Gln Thr
65                  70                  75                  80

Ser Lys Tyr Tyr Met Arg Asp Val Ile Ala Ile Glu Ser Ala Trp Leu
                85                  90                  95

Leu Glu Leu Ala Pro His Ile His Arg Ala Gly Gly Leu Phe Val Ala
            100                 105                 110

Asp Ala Ile Gln Val Gly Phe Gly Arg Ile Gly Lys His Phe Gly Tyr
        115                 120                 125

Pro Tyr Asp Val Pro Asp Tyr Ala Ser
    130                 135

<210> SEQ ID NO 22
<211> LENGTH: 333
<212> TYPE: PRT
<213> ORGANISM: Artificial Sequence
<220> FEATURE:
<223> OTHER INFORMATION: Fusion protein of Boleophthalmus pectinirostris
      FL invariant chain and multimeric antigen
<220> FEATURE:
<221> NAME/KEY: MISC_FEATURE
<222> LOCATION: (1)..(197)
<223> OTHER INFORMATION: Boleophthalmus pectinirostris FL invariant
      chain
<220> FEATURE:
<221> NAME/KEY: MISC_FEATURE
<222> LOCATION: (198)..(333)
<223> OTHER INFORMATION: Multimeric antigen

<400> SEQUENCE: 22

Met Glu His Ala Ser Glu Asp Ala Pro Leu Ala Arg Asp Ser Gly Thr
1               5                   10                  15

Gly Ser Glu Gln Ala Leu Val Val Pro Thr Ala Pro Arg Arg Gly Ser
            20                  25                  30

Asn Ser His Ala Val Lys Ile Ala Gly Ile Thr Thr Leu Val Cys Leu
        35                  40                  45

Leu Val Ser Ala Gln Val Phe Thr Ala Tyr Met Val Phe Asp Gln Lys
```

-continued

```
              50                  55                  60

Gln Gln Ile Gln Gly Leu Gln Thr Ser Asn Gln Arg Leu Glu Lys Gln
65                  70                  75                  80

Met Gly Gln Arg Pro Arg Glu Ser Leu Lys Lys Ile Val Met Pro Ala
                85                  90                  95

Asn Ser Met Pro Ile Leu Asp Phe Phe Asp Asp Gly Lys Ser Pro Gln
                100                 105                 110

Asn Ser Pro Lys Ala Glu Pro Pro Lys Gln Asp Val Ala Pro Pro Ser
        115                 120                 125

Val Glu Lys Gln Leu Gln Glu Leu Met Lys Val Phe Thr Asp Phe Pro
        130                 135                 140

Gln Met Asn Glu Ser Phe Leu Ala Asn Leu Gln Thr Met Lys Gln Lys
145                 150                 155                 160

Val Ser Glu Thr Asp Trp Lys Ser Phe Glu Ala Trp Met His Tyr Trp
                165                 170                 175

Leu Ile Phe Gln Met Ala Gln Lys Thr Ser Thr Pro Thr Pro Gln Pro
                180                 185                 190

Asp Gly Gly Ser Lys Leu Leu Pro Phe Tyr Pro Pro Asp Glu Ala Leu
        195                 200                 205

Glu Ile Gly Leu Glu Leu Asn Ser Ser Ala Leu Pro Pro Thr Ile Leu
        210                 215                 220

Pro Gln Ala Pro Ser Gly Pro Ser Tyr Ala Thr Tyr Leu Gln Pro Ala
225                 230                 235                 240

Gln Ala Gln Met Leu Thr Pro Lys Pro Leu Arg Arg Asn Asn Ser Tyr
                245                 250                 255

Thr Ser Tyr Ile Met Ala Ile Cys Gly Met Pro Leu Asp Ser Phe Arg
                260                 265                 270

Val Ile Gln Thr Ser Lys Tyr Tyr Met Arg Asp Val Ile Ala Ile Glu
                275                 280                 285

Ser Ala Trp Leu Leu Glu Leu Ala Pro His Ile His Arg Ala Gly Gly
        290                 295                 300

Leu Phe Val Ala Asp Ala Ile Gln Val Gly Phe Gly Arg Ile Gly Lys
305                 310                 315                 320

His Phe Gly Tyr Pro Tyr Asp Val Pro Asp Tyr Ala Ser
                325                 330
```

<210> SEQ ID NO 23
<211> LENGTH: 323
<212> TYPE: PRT
<213> ORGANISM: Artificial Sequence
<220> FEATURE:
<223> OTHER INFORMATION: Fusion protein of Paralichthys olivaceus FL
      invariant chain and multimeric antigen
<220> FEATURE:
<221> NAME/KEY: MISC_FEATURE
<222> LOCATION: (1)..(187)
<223> OTHER INFORMATION: Paralichthys olivaceus FL invariant chain
<220> FEATURE:
<221> NAME/KEY: MISC_FEATURE
<222> LOCATION: (188)..(323)
<223> OTHER INFORMATION: Multimeric antigen

<400> SEQUENCE: 23

```
Met Ser Glu Thr Gln Thr Leu Leu Gly Ala Pro Arg Gln Gln Thr Ala
1                   5                   10                  15

Val Asp Val Gly Ala Pro Ala Gln Gly Gly Arg Ser Ala Asn Ala Tyr
                20                  25                  30

Lys Val Val Gly Leu Thr Val Leu Ala Cys Val Leu Val Met Ser Gln
```

-continued

```
                35                40                45

Ala Met Ile Ile Tyr Phe Leu Val Asn Gln Arg Gly Asp Ile Lys Ser
    50                55                60

Leu Glu Glu Gln His Ser Gly Leu Asn Glu Gln Leu Thr Lys Gly Arg
65                70                75                80

Ser Ala Ser Met Ser Met Gln Leu Pro Ser Ser Phe His Ser Leu Thr
                85                90                95

Phe Asp Glu Lys Ser Ser Thr Arg Ala Pro Glu Glu Thr Gly Pro Pro
            100                105                110

Gln Ala Thr Gln Cys Gln Leu Glu Ala Ala Gly Glu Lys Pro Val Gln
            115                120                125

Val Pro Gly Leu Arg Pro Asp Cys Asp Glu Arg Gly Leu Tyr Arg Leu
    130                135                140

Lys Gln Cys Leu Lys His Arg Cys Trp Cys Val Asn Pro Ala Asn Gly
145                150                155                160

Glu Gln Ile Pro Gly Ser Leu Gly Lys Glu Asp Val Thr Cys Asn Lys
                165                170                175

Gly Val His Ser Val Gly Leu Asp Lys Val Leu Leu Leu Pro Phe Tyr
            180                185                190

Pro Pro Asp Glu Ala Leu Glu Ile Gly Leu Glu Leu Asn Ser Ser Ala
            195                200                205

Leu Pro Pro Thr Ile Leu Pro Gln Ala Pro Ser Gly Pro Ser Tyr Ala
    210                215                220

Thr Tyr Leu Gln Pro Ala Gln Ala Gln Met Leu Thr Pro Lys Pro Leu
225                230                235                240

Arg Arg Asn Asn Ser Tyr Thr Ser Tyr Ile Met Ala Ile Cys Gly Met
                245                250                255

Pro Leu Asp Ser Phe Arg Val Ile Gln Thr Ser Lys Tyr Tyr Met Arg
            260                265                270

Asp Val Ile Ala Ile Glu Ser Ala Trp Leu Leu Glu Leu Ala Pro His
            275                280                285

Ile His Arg Ala Gly Gly Leu Phe Val Ala Asp Ala Ile Gln Val Gly
    290                295                300

Phe Gly Arg Ile Gly Lys His Phe Gly Tyr Pro Tyr Asp Val Pro Asp
305                310                315                320

Tyr Ala Ser
```

<210> SEQ ID NO 24
<211> LENGTH: 164
<212> TYPE: PRT
<213> ORGANISM: Artificial Sequence
<220> FEATURE:
<223> OTHER INFORMATION: Fusion protein of Boleophthalmus pectinirostris
      invariant chain FRAG_A fragment and multimeric antigen
<220> FEATURE:
<221> NAME/KEY: MISC_FEATURE
<222> LOCATION: (1)..(28)
<223> OTHER INFORMATION: Boleophthalmus pectinirostris invariant chain
      FRAG_A fragment
<220> FEATURE:
<221> NAME/KEY: MISC_FEATURE
<222> LOCATION: (29)..(164)
<223> OTHER INFORMATION: Multimeric antigen

<400> SEQUENCE: 24

```
Met Asp Gln Lys Gln Gln Ile Gln Gly Leu Gln Thr Ser Asn Gln Arg
1               5                10                15

Leu Glu Lys Gln Met Gly Gln Arg Pro Arg Glu Ser Leu Leu Pro Phe
```

```
                20                    25                    30

Tyr Pro Pro Asp Glu Ala Leu Glu Ile Gly Leu Glu Leu Asn Ser Ser
            35                    40                    45

Ala Leu Pro Pro Thr Ile Leu Pro Gln Ala Pro Ser Gly Pro Ser Tyr
        50                    55                    60

Ala Thr Tyr Leu Gln Pro Ala Gln Ala Gln Met Leu Thr Pro Lys Pro
65                    70                    75                    80

Leu Arg Arg Asn Asn Ser Tyr Thr Ser Tyr Ile Met Ala Ile Cys Gly
                85                    90                    95

Met Pro Leu Asp Ser Phe Arg Val Ile Gln Thr Ser Lys Tyr Tyr Met
            100                   105                   110

Arg Asp Val Ile Ala Ile Glu Ser Ala Trp Leu Leu Glu Leu Ala Pro
        115                   120                   125

His Ile His Arg Ala Gly Gly Leu Phe Val Ala Asp Ala Ile Gln Val
        130                   135                   140

Gly Phe Gly Arg Ile Gly Lys His Phe Gly Tyr Pro Tyr Asp Val Pro
145                   150                   155                   160

Asp Tyr Ala Ser
```

```
<210> SEQ ID NO 25
<211> LENGTH: 164
<212> TYPE: PRT
<213> ORGANISM: Artificial Sequence
<220> FEATURE:
<223> OTHER INFORMATION: Fusion protein of Paralichthys olivaceus
      invariant chain fragment FRAG_A and multimeric antigen
<220> FEATURE:
<221> NAME/KEY: MISC_FEATURE
<222> LOCATION: (1)..(28)
<223> OTHER INFORMATION: Paralichthys olivaceus invariant chain fragment
      FRAG_A
<220> FEATURE:
<221> NAME/KEY: MISC_FEATURE
<222> LOCATION: (29)..(164)
<223> OTHER INFORMATION: Multimeric antigen

<400> SEQUENCE: 25
```

```
Met Asn Gln Arg Gly Asp Ile Lys Ser Leu Glu Glu Gln His Ser Gly
1               5                    10                    15

Leu Asn Glu Gln Leu Thr Lys Gly Arg Ser Ala Ser Leu Leu Pro Phe
            20                    25                    30

Tyr Pro Pro Asp Glu Ala Leu Glu Ile Gly Leu Glu Leu Asn Ser Ser
            35                    40                    45

Ala Leu Pro Pro Thr Ile Leu Pro Gln Ala Pro Ser Gly Pro Ser Tyr
        50                    55                    60

Ala Thr Tyr Leu Gln Pro Ala Gln Ala Gln Met Leu Thr Pro Lys Pro
65                    70                    75                    80

Leu Arg Arg Asn Asn Ser Tyr Thr Ser Tyr Ile Met Ala Ile Cys Gly
                85                    90                    95

Met Pro Leu Asp Ser Phe Arg Val Ile Gln Thr Ser Lys Tyr Tyr Met
            100                   105                   110

Arg Asp Val Ile Ala Ile Glu Ser Ala Trp Leu Leu Glu Leu Ala Pro
        115                   120                   125

His Ile His Arg Ala Gly Gly Leu Phe Val Ala Asp Ala Ile Gln Val
        130                   135                   140

Gly Phe Gly Arg Ile Gly Lys His Phe Gly Tyr Pro Tyr Asp Val Pro
145                   150                   155                   160

Asp Tyr Ala Ser
```

```
<210> SEQ ID NO 26
<211> LENGTH: 153
<212> TYPE: PRT
<213> ORGANISM: Artificial Sequence
<220> FEATURE:
<223> OTHER INFORMATION: Fusion protein of Boleophthalmus pectinirostris
      invariant chain fragment FRAG_B and multimeric antigen
<220> FEATURE:
<221> NAME/KEY: MISC_FEATURE
<222> LOCATION: (1)..(17)
<223> OTHER INFORMATION: Boleophthalmus pectinirostris invariant chain
      fragment FRAG_B
<220> FEATURE:
<221> NAME/KEY: MISC_FEATURE
<222> LOCATION: (18)..(153)
<223> OTHER INFORMATION: Multimeric antigen

<400> SEQUENCE: 26

Met Gln Ile Gln Gly Leu Gln Thr Ser Asn Gln Arg Leu Glu Lys Gln
1               5                   10                  15

Met Leu Leu Pro Phe Tyr Pro Pro Asp Glu Ala Leu Glu Ile Gly Leu
            20                  25                  30

Glu Leu Asn Ser Ser Ala Leu Pro Pro Thr Ile Leu Pro Gln Ala Pro
        35                  40                  45

Ser Gly Pro Ser Tyr Ala Thr Tyr Leu Gln Pro Ala Gln Ala Gln Met
    50                  55                  60

Leu Thr Pro Lys Pro Leu Arg Arg Asn Asn Ser Tyr Thr Ser Tyr Ile
65                  70                  75                  80

Met Ala Ile Cys Gly Met Pro Leu Asp Ser Phe Arg Val Ile Gln Thr
                85                  90                  95

Ser Lys Tyr Tyr Met Arg Asp Val Ile Ala Ile Glu Ser Ala Trp Leu
            100                 105                 110

Leu Glu Leu Ala Pro His Ile His Arg Ala Gly Gly Leu Phe Val Ala
        115                 120                 125

Asp Ala Ile Gln Val Gly Phe Gly Arg Ile Gly Lys His Phe Gly Tyr
    130                 135                 140

Pro Tyr Asp Val Pro Asp Tyr Ala Ser
145                 150

<210> SEQ ID NO 27
<211> LENGTH: 153
<212> TYPE: PRT
<213> ORGANISM: Artificial Sequence
<220> FEATURE:
<223> OTHER INFORMATION: Fusion protein of Paralichthys olivaceus
      invariant chain fragment FRAG_B and multimeric antigen
<220> FEATURE:
<221> NAME/KEY: MISC_FEATURE
<222> LOCATION: (1)..(17)
<223> OTHER INFORMATION: Paralichthys olivaceus invariant chain fragment
      FRAG_B
<220> FEATURE:
<221> NAME/KEY: MISC_FEATURE
<222> LOCATION: (18)..(153)
<223> OTHER INFORMATION: Multimeric antigen

<400> SEQUENCE: 27

Met Asp Ile Lys Ser Leu Glu Glu Gln His Ser Gly Leu Asn Glu Gln
1               5                   10                  15

Leu Leu Leu Pro Phe Tyr Pro Pro Asp Glu Ala Leu Glu Ile Gly Leu
            20                  25                  30

Glu Leu Asn Ser Ser Ala Leu Pro Pro Thr Ile Leu Pro Gln Ala Pro
        35                  40                  45
```

```
Ser Gly Pro Ser Tyr Ala Thr Tyr Leu Gln Pro Ala Gln Ala Gln Met
    50                  55                  60

Leu Thr Pro Lys Pro Leu Arg Arg Asn Asn Ser Tyr Thr Ser Tyr Ile
65                  70                  75                  80

Met Ala Ile Cys Gly Met Pro Leu Asp Ser Phe Arg Val Ile Gln Thr
                85                  90                  95

Ser Lys Tyr Tyr Met Arg Asp Val Ile Ala Ile Glu Ser Ala Trp Leu
            100                 105                 110

Leu Glu Leu Ala Pro His Ile His Arg Ala Gly Gly Leu Phe Val Ala
        115                 120                 125

Asp Ala Ile Gln Val Gly Phe Gly Arg Ile Gly Lys His Phe Gly Tyr
        130                 135                 140

Pro Tyr Asp Val Pro Asp Tyr Ala Ser
145                 150

<210> SEQ ID NO 28
<211> LENGTH: 16
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (9)..(9)
<223> OTHER INFORMATION: Xaa is H or N
<220> FEATURE:
<221> NAME/KEY: MISC_FEATURE
<222> LOCATION: (11)..(11)
<223> OTHER INFORMATION: Xaa is G or N
<220> FEATURE:
<221> NAME/KEY: MISC_FEATURE
<222> LOCATION: (13)..(13)
<223> OTHER INFORMATION: Xaa is N or Q
<220> FEATURE:
<221> NAME/KEY: MISC_FEATURE
<222> LOCATION: (14)..(14)
<223> OTHER INFORMATION: Xaa is E or A
<220> FEATURE:
<221> NAME/KEY: MISC_FEATURE
<222> LOCATION: (15)..(15)
<223> OTHER INFORMATION: Xaa is Q or E
<220> FEATURE:
<221> NAME/KEY: MISC_FEATURE
<222> LOCATION: (16)..(16)
<223> OTHER INFORMATION: Xaa is L or M

<400> SEQUENCE: 28

Asp Ile Lys Ser Leu Glu Glu Gln Xaa Ser Xaa Leu Xaa Xaa Xaa Xaa
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Generic sequence
<220> FEATURE:
<221> NAME/KEY: MISC_FEATURE
<222> LOCATION: (4)..(4)
<223> OTHER INFORMATION: Xaa is G or D
<220> FEATURE:
<221> NAME/KEY: MISC_FEATURE
<222> LOCATION: (7)..(7)
<223> OTHER INFORMATION: Xaa is T or A
<220> FEATURE:
<221> NAME/KEY: MISC_FEATURE
<222> LOCATION: (8)..(8)
<223> OTHER INFORMATION: Xaa is T or S
<220> FEATURE:
```

```
<221> NAME/KEY: MISC_FEATURE
<222> LOCATION: (12)..(12)
<223> OTHER INFORMATION: Xaa is L or M
<220> FEATURE:
<221> NAME/KEY: MISC_FEATURE
<222> LOCATION: (16)..(16)
<223> OTHER INFORMATION: Xaa is M or V

<400> SEQUENCE: 29

Gln Ile Gln Xaa Leu Gln Xaa Xaa Asn Gln Arg Xaa Glu Lys Gln Xaa
1               5                   10                  15

<210> SEQ ID NO 30
<211> LENGTH: 11
<212> TYPE: PRT
<213> ORGANISM: Artificial Sequence
<220> FEATURE:
<223> OTHER INFORMATION: Influenza tag

<400> SEQUENCE: 30

Gly Tyr Pro Tyr Asp Val Pro Asp Tyr Ala Ser
1               5                   10
```